(12) United States Patent
Berlinger et al.

(10) Patent No.: US 9,855,443 B2
(45) Date of Patent: Jan. 2, 2018

(54) DETERMINING SOFT-TISSUE SHIFT TAKING INTO ACCOUNT BONY SHIFT

(71) Applicant: Brainlab AG, Munich (DE)

(72) Inventors: Kajetan Berlinger, Munich (DE); Cornel Schlossbauer, Alling (DE); Joerg Rehs, Munich (DE); Stephan Elsner, Munich (DE)

(73) Assignee: Brainlab AG, Munich (DE)

( * ) Notice: Subject to any disclaimer, the term of this patent is extended or adjusted under 35 U.S.C. 154(b) by 256 days.

(21) Appl. No.: 14/759,906

(22) PCT Filed: May 7, 2013

(86) PCT No.: PCT/EP2013/059449
§ 371 (c)(1),
(2) Date: Jul. 8, 2015

(87) PCT Pub. No.: WO2014/108217
PCT Pub. Date: Jul. 17, 2014

(65) Prior Publication Data
US 2015/0367146 A1    Dec. 24, 2015

Related U.S. Application Data

(63) Continuation-in-part of application No. PCT/EP2013/050240, filed on Jan. 9, 2013.

(51) Int. Cl.
*A61N 5/10* (2006.01)
*A61B 6/04* (2006.01)
(Continued)

(52) U.S. Cl.
CPC ............ *A61N 5/1049* (2013.01); *A61B 6/032* (2013.01); *A61B 6/04* (2013.01); *A61B 6/4085* (2013.01);
(Continued)

(58) Field of Classification Search
CPC ......................................... A61N 5/103–5/1075
See application file for complete search history.

(56) References Cited

U.S. PATENT DOCUMENTS 6,661,870 B2    12/2003 Kapatoes et al.
7,567,694 B2    7/2009 Lu et al.
(Continued)

FOREIGN PATENT DOCUMENTS

EP          1384494        5/2005
WO          2012095172     7/2012

OTHER PUBLICATIONS

European Patent Office, International Search Report of PCT/EP2013/059449 dated Jun. 20, 2013, pp. 1-4, European Patent Office, Rijswijk, Netherlands.
(Continued)

*Primary Examiner* — Charles A Marmor, II
*Assistant Examiner* — Thaddeus Cox
(74) *Attorney, Agent, or Firm* — Middleton Reutlinger

(57) ABSTRACT

A medical data processing method for determining a change in the position of a soft tissue body part of a patient's body, the data processing method being constituted to be executed by a computer and comprising the following steps: a) acquiring (S10, S20) bony body part planned position data comprising bony body part planned position information describing a planned position of a bony body part of the patient's body; b) acquiring (S10, S20) soft tissue body part planned position data comprising soft tissue body part planned position information describing a planned position of the soft tissue body part; c) acquiring (S11, S21) bony body part actual position data comprising bony body part actual position information describing an actual position of the bony body part; d) acquiring (S11, S21) soft tissue body
(Continued)

part actual position data comprising soft tissue body part actual position information describing an actual position of the soft tissue body part; e) determining (S12, S22), based on the bony body part planned position data and the bony body part actual position data, bony body part position transformation data comprising bony body part position transformation information describing a bony body part position transformation between the planned position and the actual position of the bony body part; f) determining (S13, S23), based on the bony body part position transformation data and the soft tissue body part actual position data, soft tissue transformed actual position data comprising soft tissue transformed actual position information describing a transformed actual position of the soft tissue body part; g) determining (S14, S24), based on the soft tissue transformed actual position data and the soft tissue body part planned position data, soft tissue body part position transformation data comprising soft tissue body part position transformation information describing a soft tissue body part position transformation between the planned position of the of the soft tissue body part and the transformed actual position of the soft tissue body part.

14 Claims, 2 Drawing Sheets

(51) Int. Cl.
*A61B 6/03* (2006.01)
*A61B 6/00* (2006.01)
*G06T 7/00* (2017.01)
*G06T 7/30* (2017.01)

(52) U.S. Cl.
CPC ........... *A61N 5/107* (2013.01); *A61N 5/1037* (2013.01); *A61N 5/1071* (2013.01); *A61N 5/1077* (2013.01); *G06T 7/0012* (2013.01); *G06T 7/30* (2017.01); *A61N 2005/1061* (2013.01); *A61N 2005/1062* (2013.01); *A61N 2005/1072* (2013.01); *A61N 2005/1074* (2013.01); *G06T 2207/10072* (2013.01)

(56) References Cited

U.S. PATENT DOCUMENTS

| | | | |
|---|---|---|---|
| 2008/0002811 A1 | 1/2008 | Allison | |
| 2012/0008735 A1* | 1/2012 | Maurer | G06T 7/0014 378/5 |
| 2012/0114208 A1 | 5/2012 | Hirasawa et al. | |
| 2013/0101082 A1* | 4/2013 | Jordan | A61B 6/4035 378/19 |
| 2013/0287167 A1* | 10/2013 | Gum | A61N 5/1049 378/20 |

OTHER PUBLICATIONS

Yeung, et al., "Tumor Localization Using Cone-Beam CT Reduces Setup Margins in Conventionally Fractionated Radiotherapy for Lung Tumors", International Journal of Radiation: Oncology Biology Physics, Pergamon Press, USA, vol. 74, No. 4, Jul. 15, 2009, pp. 1100-1107.

* cited by examiner

DETERMINING SOFT-TISSUE SHIFT TAKING INTO ACCOUNT BONY SHIFT

The present invention is directed to a method, in particular a medical data processing method, for determining a shift in the position of a soft tissue body part of a patient's body, in accordance with claim 1, a corresponding program and computer running that program as well as a radiotherapy system comprising that computer. Furthermore, the invention is directed to a medical data processing method of assessing a distribution of an irradiation dose which involves the method for detecting a shift in the position of a soft tissue body part, and a data processing method of controlling a radiotherapy system which involves the medical data processing method of assessing a distribution of an irradiation dose.

When conducting radiotherapy on an irradiation target such as a tumour located in soft tissue of a patient's body, a problem often raises that the soft tissue may have changed its position between in a point in time at which the radiotherapy procedure was planned and a point in time at which the patient was placed ready for radiotherapy. As a consequence, not only the soft tissue body part comprising the target region but also other soft tissue body parts may have changed their position. This may result in the target region no longer being covered by the beam of treatment radiation and rather other body parts being in the beam direction. This may result in undesired irradiation of body parts such as organs at risk (OARs), irradiation of which should be avoided as far as possible in order to avoid detrimental effects on the patient's health.

Known solutions to this problem include for example fusing a volume scan (e.g. a CBCT scan) of the patient acquired after he has been placed ready for treatment to a previously generated computer tomography on the basis of which tomography the radiotherapy procedure was planned. If it is determined that the position of the target region differs between the two different image sets, the dose distribution is recalculated based on the current position of the patient in which he has been placed ready for treatment. This, however, involves great computational effort and time and thus is costly. Furthermore, recalculating the dose distribution might not be necessary since, despite a difference in position of the target region between the image set used for planning and the image set generated after placing the patient ready for treatment, the actual position of the target region after placing the patient may still be within acceptable limits compared to the planned position. It may then be possible to conduct the envisaged radiotherapy procedure without recalculating the dose distribution.

The problem to be solved by the invention thus is to provide in particular a way of determining whether a change in the position of a target region requires recalculation of the planned dose distribution.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

EXEMPLARY SHORT DESCRIPTION OF THE PRESENT INVENTION

In this chapter, the invention shall be described in general terms without limiting the invention to the features described in this chapter.

The invention is generally directed to a medical data processing method in which a shift between a planned and an actual position of a bony body part is determined. Furthermore, medical image data is acquired which describes an actual position of a soft tissue body part. The position of the soft tissue body part is corrected in particular by applying the shift between the planned and the actual positions of the bony body part to the actual position of the soft tissue body part. Thereby, a transformed (in particular corrected) actual position of the soft tissue body part is determined, on the basis of which a shift between the planned position of the soft tissue body part and the transformed actual position of the soft tissue body part is determined. Thereby, a net shift in the position of the soft tissue body part which has been corrected for a shift of the bony body part is determined and it can then be determined whether this net shift is within predetermined limits. If the net shift is within those limits, it is decided to not re-calculate the dose distribution. Rather, radiation therapy is then started. If the shift is outside of the limits, the dose distribution is re-calculated.

The invention is also directed to a medical data processing method of assessing a distribution of a radiation dose which is based on the medical data processing method for determining a shift in the position of a soft tissue body part and involves steps which allow to determine whether the dose distribution has to be re-calculated.

Furthermore, the invention is directed to a data processing method of controlling a radiotherapy system which involves the medical data processing method of assessing a dose distribution. In particular, the method of controlling a radiotherapy system is directed to generating a start signal for radiotherapy if it is determined that the dose distribution need not be re-calculated.

GENERAL DESCRIPTION OF THE INVENTION

In this chapter, the invention is described with general reference to its preferred features which may be combined with one another as appears feasible from the skilled person's point of view.

The invention is directed to in particular a method, more particularly to a medical data processing method, for determining a change (in particular a shift) in the position of a soft tissue body part of a patient's body, which method is preferably constituted to be executed by a computer. A soft tissue body part is understood to be in particular an anatomical structure which comprises soft tissue such as an internal organ (for example, the colon or the liver, the brain, the skin or a muscle). In particular, the soft tissue body part does not comprise any hard tissue such as a bony structure or cartilage. Soft tissue body parts are known to generally be able to change their position relative to for example bony body parts. The method further preferably comprises the following steps.

Preferably, bony body part planned position data is acquired which comprises bony body part planned position information. The bony body part planned position information describes in particular a planned position of a bony body part of the patient's body. The bony body part planned position data is in particular predetermined, i.e. generated at a point in time before and outside of execution of the inventive method. For example, the bony body part planned position data is acquired based on (in particular, from) medical image data taken with a computer tomograph. The bony body part is in particular an anatomical structure which is not soft tissue, more particularly, it comprises (in particular, consists of) bony tissue or cartilage.

Preferably, soft tissue body part planned position data is acquired which comprises soft tissue body part planned position information. The soft tissue body part planned position information describes in particular a planned position of the soft tissue body part. The soft tissue body part planned position data is preferably also predetermined in the sense described above with regard to the bony body part planned position data. The soft tissue planned position data is preferably also acquired based on (in particular, from) medical image data taken with a medical imaging apparatus such as a medical resonance tomograph (MRT) or a computer tomograph (CT), i.e. based on a MR tomography or a computed tomography.

The bony body part planned position information describes the planned position of the bony body part in particular relative to a beam arrangement or in a global reference system in which also the position of the beam arrangement is defined. The soft tissue body part planned position information describes the planned position of the soft tissue body part in particular relative to the planned position of the bony body part in particular relative to the planned position of the bony body part or relative to the beam arrangement. Alternatively or additionally, the planned position of the soft tissue body part may be described in a global coordinate system in which also the planned position of the bony body part and the position of the beam arrangement are defined.

Preferably, the planned position of the bony body part and the planned position of the soft tissue body part serve as a basis in particular for generating a predetermined treatment plan which comprises information supporting execution of radiotherapy treatment on the patient's body, in particular on a target region comprising a treatment body part which is to be treated by the envisaged medical procedure (in particular by radiotherapy). The target region shall be in particular treated by the envisaged medical procedure—if this procedure encompasses radiotherapy, the target region shall lie in particular in a beam direction (in particular, it shall be covered by the beam arrangement) and for example be irradiated with treatment radiation. In particular, the soft tissue body part comprises the target region. However, the target region may also be located in other parts of the patient's body, in particular in parts being near to, in particular adjacent to, the soft tissue body part. The soft tissue body part may also be part of a risk region (for example, it may be at least part of an organ at risk, for example the colon or the stomach), irradiation of which is undesirable during the envisaged radiotherapy procedure (which may be directed to a treatment body part comprising, for example, the prostate). Such a treatment plan generally comprises information about the position of the target region in the patient's body, the doses to be applied to specific regions of the patient's body and preferably also information about the positions of organs at risk. Furthermore, the treatment plan preferably also comprises information about the beam geometry, in particular of the cross-section, of the treatment beam (in particular, of the beam arrangement). The treatment beam is a beam of treatment radiation which is in particular ionizing radiation (for example, hard x-rays or gamma-rays emitted from a particle accelerator or another source of high-energy, in particular ionizing, electromagnetic radiation such as a radioisotope). Furthermore, the treatment plan comprises in particular information about the length of time of each treatment session and information about the intervals between individual treatment sessions. In particular, the treatment plan comprises planned dose distribution data comprising planned dose distribution information. The planned dose distribution information describes in particular a planned distribution (in particular a planned spatio-temporal distribution, more particularly spatial distribution) of an irradiation dose to be applied to and/or to be accumulated in the patient's body. In particular, it describes an irradiation dose in the patient's body which is achieved when irradiating the patient when the soft tissue body part has its planned position.

Preferably, bony body part actual position data is acquired which comprises bony body part actual position information. The bony body part actual position information describes in particular an actual position of the bony body part in particular relative to the position of the beam arrangement or in a global coordinate system in which also the position of the beam arrangement is defined. The bony body part attains the actual position in particular when the patient has been placed ready for radiotherapy, for example when the patient has been laid onto a patient positioning device such as a couch on which he is to be irradiated. The bony body part actual position data is preferably acquired based on (in particular, from) medical image data taken with a cone-beam computer tomograph (i.e. from a cone-beam computer tomography) or with an x-ray device (i.e. from a two-dimensional x-ray image).

Preferably, soft tissue body part actual position data is acquired which comprises soft tissue body part actual position information. The soft tissue body part actual position information describes in particular an actual position of the soft tissue body part in particular relative to the actual position of the bony body part or relative to the beam arrangement. Alternatively or additionally, the soft tissue body part actual position information describes the actual position of the soft tissue body part in a global reference system in which the actual position of the bony body part or the position of the beam arrangement is defined. The soft tissue body part attains its actual position in particular when the patient has been placed ready for radiotherapy as described above with regard to the actual position of the bony body part (therefore, in particular when the bony body part is in its actual position). The soft tissue body part actual position data is acquired preferably based on (in particular, from) medical image data taken with a cone-beam computer tomograph (i.e. from a cone-beam computer tomography).

Preferably, bony body part position transformation data comprising body part position transformation information is determined based on the body part planned position data (in particular based on the bony body part planned position information) and the bony body part actual position data (in particular the bony body parts actual position information). The bony body part position transformation information describes in particular a bony body part position transformation between the planned position and the actual position of the bony body part. Within the context of this disclosure, transformations are understood to be functions, in particular linear functions, which describe a transformation, in particular a mapping, between positions (in particular, between coordinates and/or coordinate systems). In particular, a transformation is understood to be determined based on the result of a fusion function, in particular it is understood to be a fusion function (in particular an image fusion function).

Preferably, a transformation is a rigid transformation, i.e. describes in particular a rigid fusion between in particular image features. A rigid transformation matches image features onto one another without deforming them, in particular a rigid transformation is also known as a 6 DOF-fusion which describes 6 degrees of freedom (three degrees of translation and three degrees of rotation) when assessing three-dimensional images for example, image features are mapped onto each other which fulfill a predetermined level of (in particular geometric) similarity and in the end are laid over one another without adapting their geometries to one another (in particular, without deforming them). Thereby, the position of a specific image feature in one image can be determined for the same image feature in another image in a simple manner which is robust and reliable enough to conduct the envisaged radiotherapy procedure on the basis of such image comparison. Alternatively, a transformation may be understood to bean elastic fusion transformation. In that case, however, higher computational effort may be required in particular to separate image information describing the soft tissue body part from image information describing the bony body part.

Preferably, soft tissue transformed actual position data comprising soft tissue transformed actual position information is determined based on the bony body part position transformation data (in particular the bony body position transformation information) and the soft tissue body part actual position data (in particular the soft tissue body part actual position information). The soft tissue transformed actual position information describes in particular a transformed actual position of the soft tissue body part. The transformed actual position of the soft tissue body part is determined in particular by applying the bony body part position transformation to the soft tissue body part actual position information (i.e. to the actual position of the soft tissue body part). As noted above, the soft tissue body part position transformation can be a rigid transformation or an elastic transformation (i.e. an elastic fusion transformation).

Preferably, soft tissue body part position transformation data comprising soft tissue body part position transformation information is determined based on the soft tissue transformed actual position data (in particular the soft tissue transformed actual position information) and the soft tissue body part planned position data (in particular the soft tissue body part planned position information). The soft tissue body part position transformation information describes in particular a soft tissue body part position transformation between the planned position of the soft tissue body part and the transformed actual position of the soft tissue body part. As explained above, the soft tissue body part position transformation can be a rigid transformation or an elastic transformation. The soft tissue body part position transformation data is in particular determined by determining a soft tissue body part position transformation which transforms, in particular maps, the planned position of the soft tissue body part onto the transformed actual position of the soft tissue body part.

Determining the soft tissue body part position transformation in this way means in particular to determine a mapping between the planned position and the transformed actual position of the soft tissue body part, in which mapping a positional shift of the bony body part between the point in time at which the bony body part planned position data was generated and the point in time at which the bony body part actual position data was acquired is already accounted for. Thereby, a shift in the position of the soft tissue body part between the point in time at which the soft tissue body part planned position data (in particular the medical image data serving as its basis) was acquired and the point in time at which the soft tissue body part actual position data (in particular the medical image data serving as its basis) was acquired is determined which describes a positional shift of the soft tissue body part in particular relative to the position of the beam arrangement. Advantageously, both the bony body parts actual position data and the soft tissue body part actual position data is acquired based on a cone-beam computer tomography. Thereby, only a single set of images describing the actual positions of the bony body part and the soft tissue body part has to be generated which saves time. This reduces the dose administered to the patient's body compared to known approaches which involve using multiple imaging modalities and further sets of images.

The invention is also directed to a method of assessing a distribution of an irradiation dose which is in particular based on the aforementioned method steps and their features. In particular, it is determined whether an irradiation dose administered to the patient's body by irradiating it with treatment radiation under the assumption that the soft tissue body part has its transformed actual position) is distributed in accordance with the dose distribution described by the treatment plan (which was generated under the assumption that the soft tissue body part has its planned position). To this end, preferably actual dose distribution data is determined comprising actual dose distribution information which describes an actual distribution of the irradiation dose in the patient's body when the soft tissue body part has its transformed actual position. According to one embodiment of the invention, it is then preferably determined whether the actual dose distribution fulfills a predetermined condition. This predetermined condition describes in particular whether a body part contained in the target region (which may be the soft tissue body part or, as described above, another part of the patient's body) is covered by the beam arrangement, i.e. whether it will be irradiated if the soft tissue body part has its transformed actual position. For example, a difference between the planned position and the transformed actual position of the soft tissue body part (more generally, a movement of the soft tissue body part) may lead to a movement of other body parts neighbouring (in particular, lying adjacent to) the soft tissue body part. Furthermore, it is in particular determined whether a body part which shall not be irradiated with treatment radiation such as organs at risk are covered by the beam arrangement, i.e. whether they would be irradiated with treatment radiation if radiotherapy is started while the soft tissue body part has its transformed actual position. It therefore is advantageous to generate the soft tissue body part actual position data based on a cone-beam computed tomography of the soft tissue body part since the corresponding image information will contain information about the absorbance of treatment radiation by the soft tissue body part and the other body parts which shall not be irradiated. This absorbance is then described in particular by Hounsfield units (HU). Based on such information about the absorbance, the actual dose distribution can be determined.

According to another embodiment of the medical data processing method of assessing a distribution of an irradiation dose, preferably planned dose distribution is acquired which comprises planned dose distribution information. The planned dose distribution information describes in particular a planned distribution of an irradiation dose in the patient's body under the assumption that the soft tissue body part has its planned position (in particular, when the soft tissue body part has its planned position). In particular, the bony body part has its planned position when the soft tissue body part has its planned position. The planned dose distribution data is in particular described by the aforementioned treatment plan. Furthermore, preferably the actual dose distribution data described above is determined. It may then preferably be determined whether a difference between the planned dose distribution and the actual dose distribution fulfills a predetermined condition. This determination is in particular based on comparing the planned dose distribution information and the actual dose distribution information. The predetermined condition describes in particular an average difference in the treatment radiation dose administered to a patient's body part in consideration of both the target region and regions which shall not be irradiated as explained above. Preferably, the predetermined condition is defined as a difference between a planned distribution of an irradiation dose and an actual distribution of an irradiation dose not exceeding a predetermined value. Preferably, the planned dose distribution is updated based on the soft tissue body part position transformation data if it is determined and the predetermined condition is not fulfilled. In particular, the soft tissue body part position transformation is applied to the positional information (and preferably therefore also to the dose values associated with the positions described by that positional information) contained in the planned dose distribution data in order to map the planned distribution of the irradiation dose onto the transformed actual position of the soft tissue body part. Thereby, the planned distribution is adapted to the change in position of body parts which is due to the shift in position of the soft tissue body part.

In both of the above-described embodiments of the medical data processing method of assessing a distribution of an irradiation dose, preferably at least one of the soft tissue body part position transformation data and the soft tissue transformed actual position data is saved in a non-volatile memory device which is in particular an electronic, more particularly a digital memory device. This is in particular done if it is determined that the predetermined condition is fulfilled, i.e. in particular in case of it being determined that the positional shift of the soft tissue body part does not require an update of the treatment plan, in particular of the planned dose distribution data. Saving the respective data supports re-use of the respective data in future treatment sessions (also called fractions).

Alternatively or additionally to updating the planned dose distribution data, the patient's body (in particular the soft tissue body part) may be moved in particular relative to the position of the beam arrangement. This movement is in particular conducted based on the soft tissue body part position transformation data. For example, the soft tissue body part position transformation serves as a basis for determining patient positioning device control data comprising patient positioning device control information. The patient positioning device control information describes in particular (preferably electronic, in particular digital) control signals which are issued to a moving unit (such as a motor) of a patient positioning device (such as a couch on which the patient is placed for radiotherapy) in the directions (or the inverse directions, respectively) described by the soft tissue body part position transformation. In particular, the patient's body is moved by an amount corresponding to the inverse of the positional net shift of the soft tissue body part.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The present invention is also directed to radiotherapy system which comprises the above-mentioned computer. Furthermore, the radiotherapy system comprises preferably the treatment device. Preferably, the treatment system comprises a patient positioning device for positioning the patient's body such as a couch for placing the patient thereon. The treatment device is preferably constituted to treat the treatment body part if the patient is positioned (in particular, placed on the couch) for treatment. In particular, the treatment device is constituted so that the relative positions between the beam arrangement (in particular the beam positions) relative to the treatment device are controllable (in particular settable) so that an arrangement of beam positions can be set, the relative positions of the set arrangement corresponding preferably to (in particular are identical with) the relative positions between the beam positions which are in accordance with the treatment plan, in particular the planned distribution of the irradiation dose. In particular the patient positioning device and the treatment device are constituted so that the relative position between the set arrangement of beam positions and the treatment body part is changeable.

Preferably, the treatment system comprises a medical imaging device such as a CBCT-device. Optionally, the treatment system comprises a second (other) medical imaging device such as an x-ray device for generating two-dimensional x-ray images. The CBCT-device is constituted to generate the three-dimensional CBCT images. In particular, the computer comprises a database within which the relative position between the CBCT image generated by the CBCT-device and a reference system of the treatment device is known. Preferably, the relationship between a reference system within which the beam arrangement is set and the reference system of the CBCT image is stored in the database and/or is determinable based on the data stored in the database of the computer and based on data describing the set beam arrangement.

According to an embodiment, x-ray images can be generated by means of the CBCT-device. According to another embodiment, an x-ray device (which is independent from the CBCT-device) is part of or associated with/attached to the radiotherapy system and is used for generating two-dimensional x-ray images. Preferably, the database of the computer stores a positional relationship between CBCT and/or the x-ray imaging geometry (or CBCT and/or x-ray imaging geometries) and reference system of the CBCT-image and/or a reference system within which the position of the beam arrangement is set. Preferably, after setting the beam arrangement, the relative beam positions defined by the arrangement are fixed with respect to each other but, according to an embodiment, the position of the set beam arrangement can be determined with respect to the treatment device. The beam arrangement is set in particular in accordance with control data (called arrangement control data which are provided (in particular received)). The arrangement control data can be set by an operator to comply as best as possible with the planned relative position under the assumption of an assumed position of the treatment body part (after positioning the patient ready for radiotherapy on the couch). The arrangement control data defines a position of the beam arrangement in the reference system of the beam arrangement.

In particular, the invention does not involve, in particular it does not comprise or encompass, an invasive step which would represent a substantial physical interference with the body requiring professional medical expertise to be carried out and entailing a substantial health risk even when carried out with the required professional care and expertise. In particular, the invention does not comprise a step of placing the medical implant in position for fastening it to the anatomical structure or a step of fastening the medical implant to the anatomical structure or a step of preparing the anatomical structure for being fastened to the medical implant. More particularly, the invention does not involve (in particular comprise or encompass) any surgical or therapeutic activity. Rather, the invention is directed to in particular processing digital data such as medical image data and controlling a device based on the result of such processing. For at least this reason, no surgical or therapeutic activity (in particular no surgical or therapeutic step) is necessitated or implied by carrying out the invention.

Definitions

In this chapter, definitions are disclosed for terminology used in the present disclosure. These definitions also form part of the present disclosure.

A treatment body part can be treated by one or more treatment beams issued from one or more directions at one or more times. Thus the treatment by means of the at least one treatment beam follows a spatial pattern and a time pattern. To cover the spatial and time features of the treatment by means of the at least one treatment beam, the term "beam arrangement" is used. The beam arrangement is an arrangement of at least one treatment beam.

The beam positions describe the positions of the treatment beams of the beam arrangement. The arrangement of beam positions is called positional arrangement. A beam position is preferably defined by the beam direction and additional information which allows to assign a specific location in particular a three-dimensional space to the treatment beam, for example information about the coordinates in a defined coordinate system. The specific location is one point on preferably a straight line. This line is called "beam line" and runs in the beam direction and for instance runs along the central axis of the treatment beam. The defined coordinate system is preferably defined relative to the treatment device or relative to at least part of the patient's body. The positional arrangement comprises (in particular consists of) at least one beam position, in particular a discrete set of beam positions (e.g. two or more different beam positions) or a continuous multiplicity (manifold) of beam positions.

During treatment, at least one (i.e. one or more) treatment beam adopts in particular the treatment beam positions defined by the positional arrangement simultaneously or sequentially (the latter in particular in case there is just one beam source to emit a treatment beam). If there are several beam sources, at least a sub-set of all beam positions can also be adopted simultaneously by treatment beams during the treatment. In particular one or more sub-sets of the treatment beams can adopt the beam positions of the arrangement in accordance with a pre-defined sequence. A sub set of treatment beams comprises one or more treatment beams. The full set of treatment beams which comprise one or more treatment beams and which adopts all beam positions defined by the positional arrangement is the beam arrangement.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The information on the imaging geometry preferably comprises information which allows the analysis image (x-ray image) to be calculated, given a known relative position between the imaging geometry analysis apparatus and the analysis object (anatomical body part) to be analysed by the x-ray radiation, if the object (anatomical body part) to be analysed is known, wherein "known" means that the spatial geometry (size and shape) of the analysis object is known. This means in particular that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The position and in particular orientation of the imaging geometry is in particular defined by the position of the x-ray device, in particular by the position of the x-ray source and the x-ray detector and/or in particular by the position of the multiplicity (manifold) of x-ray beams which pass through the analysis object and are detected by the x-ray detector. The imaging geometry in particular describes the position (in particular, the orientation) and the shape (for example, a conical shape exhibiting a specific angle of inclination) of said multiplicity (manifold). The position can in particular be represented by the position of an x-ray beam which passes through the centre of said multiplicity or by a position of a geometric object (such as a truncated cone) which represents the multiplicity (manifold) of x-ray beams. Information concerning the above-mentioned interaction is preferably three-dimensionally known, for example from a three-dimensional CT, and describes the interaction in a spatially resolved way for points and/or regions of the analysis object, in particular force all of the points and/or regions of the analysis object. Knowledge of the imaging geometry in particular allows a location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made in particular to the following publications:

1. "An Efficient and Accurate Camera Calibration Technique for 3D Machine Vision", Roger Y. Tsai, Proceedings of the IEEE Conference on Computer Vision and Pattern Recognition. Miami Beach, Fla., 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344. See also http://www.cs.cmu.edu/~rgw/TsaiDesc.html
3. Publication by Ziv Yaniv, "Fluoroscopic X-ray Image Processing and Registration for Computer-Aided Orthopedic Surgery"
4. EP 08 156 293.6
5. U.S. 61/054,187

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information". Where in the context of this disclosure it is said that certain data or information forms a basis for determining other data or information, it is to be understood that this encompasses determining the other data or information from the certain data or information. Where in the context of this disclosure it is said that information is information about a specific entity, this encompasses the case of the information describing, in particular representing, that entity.

In this application, the term "image morphing" is also used as an alternative to the term "image fusion", but with the same meaning.

Elastic fusion transformations (e.g. image fusion transformation) are in particular designed to enable a seamless transition from one data set (e.g. first data set, e.g. first image) to another data set (e.g. second data set, e.g. second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighbouring voxels. Due in particular to a high number of (iteration) steps, large deformations can be implemented.

The determined elastic fusion transformation can be in particular used to determine a degree of similarity (similarity measure also referred to as "measure of similarity") between the first and second data set (first and second image). To this end, the deviation of the elastic fusion transformation and an identity transformation is determined. The degree of deviations can be for instance calculated by determining the difference between the determinant of the elastic fusion transformation and the identity transformation. The higher the deviation, is the less is the similarity. Thus, the degree of deviation can be used to determine a measure of similarity.

A measure of similarity can in particular be determined on the basis of a determined correlation between the first and second data set.

DESCRIPTION OF THE FIGURES

In the following, specific embodiments of the invention are disclosed with reference to the figures which are to be understood as mere examples without limiting effect to the scope of the invention.

Figure 1:
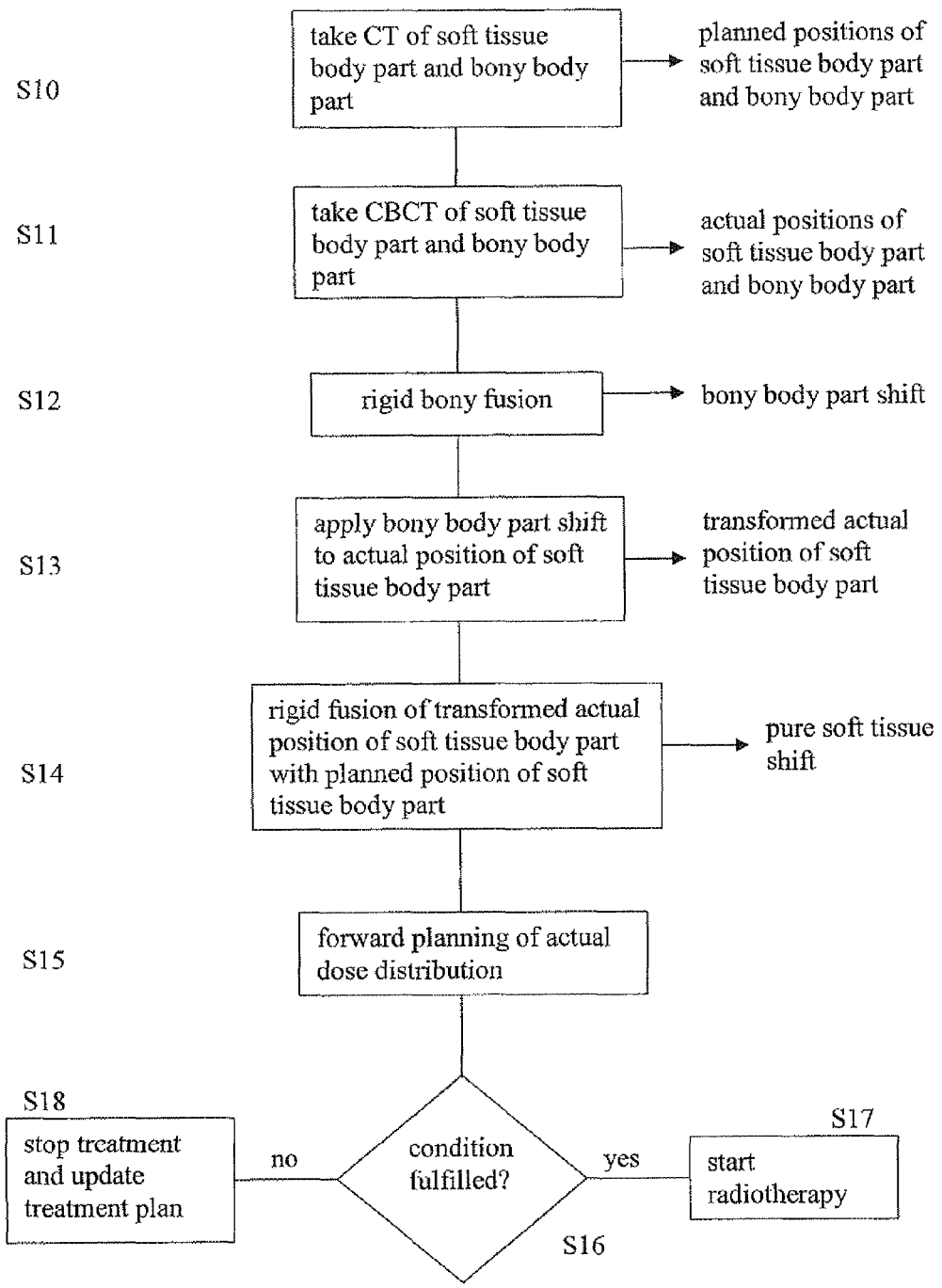
FIG. 1 shows an algorithm for determining whether the treatment plan needs to be updated or whether radiotherapy can be started.

The algorithm of FIG. 1 starts with step S10 in which a computer tomography (CT) is taken of both the soft tissue body part and the bony body part. The computer tomography serves as a basis for generating the bony body part planned position data and the soft tissue body part planned position data. Step S10 therefore leads to information about the planned positions of the soft tissue body part and the bony body part.

The algorithm then continues with step S11 in which a cone-beam computed tomography (CBCT) is taken of the soft tissue body part and the bony body part. The CBCT serves as a basis for generating the bony body part actual position data and the soft tissue body part actual position data. Thereby, step S11 leads to information about the actual positions of the soft tissue body part and the bony body part.

In subsequent step S12, a rigid bony fusion is conducted, i.e. the planned position of the bony body part is fused with the actual position of the bony body part. Thereby, step S12 leads to information about the positional shift of the bony body part (bony body part shift) which is represented by the bony body part position transformation information.

The method then continues with step S13 in which the bony body part shift is applied to the actual position of the soft tissue body part in order to determine the soft tissue transformed actual position information. In step S14, a rigid fusion is then conducted of the transformed actual position of the soft tissue body part with the planned position of the soft tissue body part, whereby the pure soft tissue shift (in this disclosure also described as a net shift in the position of the soft tissue body part) is determined. The pure soft tissue shift is represented by the soft tissue body part position transformation.

The pure soft tissue shift then serves as a basis for forward planning of the actual dose distribution in step S15, i.e. of the dose distribution which would be administered to the patient with the soft tissue body part having the actual position. This step therefore comprises in particular acquiring the actual dose distribution data and preferably the planned dose distribution data.

In step S16 it is then determined whether the actual dose distribution fulfills the predetermined condition. For example, step S16 determines whether organs at risk are covered by the beam arrangement or whether the treatment target would receive the required radiation dose if irradiated at that moment.

If it is determined in step S16 that the condition is fulfilled, radiotherapy is started in step S17 in particular by determining irradiation control data and issuing a corresponding signal to a radiation treatment device. Preferably, the information about the pure soft tissue shift is then saved for future treatment planning on the respective patient.

If step S16 determines that the condition is not fulfilled, treatment is stopped at step S18 and the treatment plan is updated on the basis of the soft tissue body part having the transformed actual position. Optionally, the information about the pure soft tissue shift can then also be stored for future use.

Figure 2:
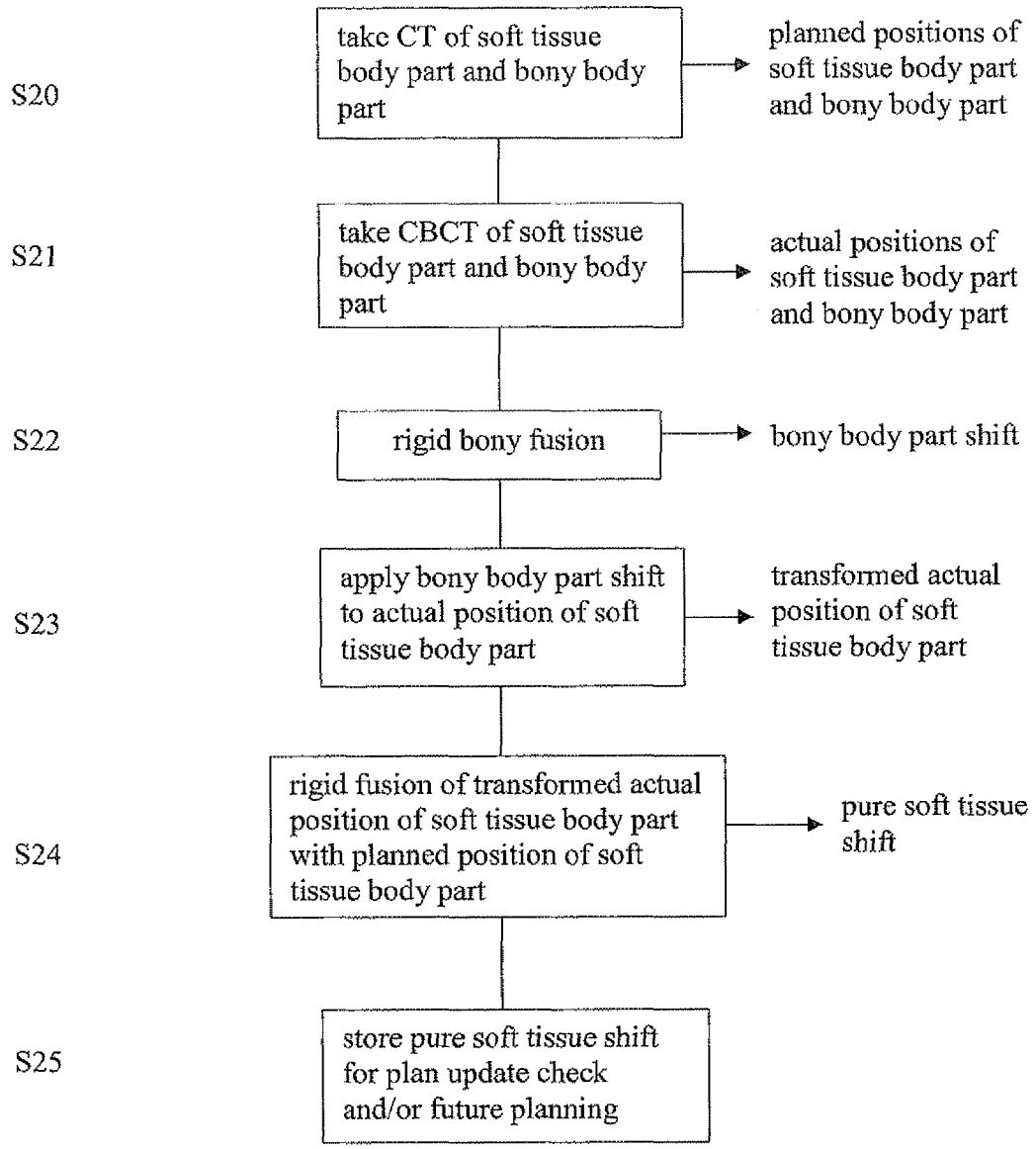
FIG. 2 shows in algorithm in which the determined positional shift of the soft tissue body part is stored for future use.

FIG. 2 shows an adaption of the algorithm of FIG. 1, wherein steps S20 to S24 correspond to steps S10 to S14 of FIG. 1. The algorithm of FIG. 2 then continues with step S25 in which the pure soft tissue shift is stored for a cheek whether the treatment plan needs to be updated ("plan update check") and/or for future treatment planning. Steps S20 to S25 are preferably executed before the patient undergoes radiotherapy. More preferably, steps S20 to S25 are executed for, in particular during positioning of the patient on a couch of the radiotherapy system, in particular while the patient is being properly positioned relative to the position of the beam arrangement.

Radiotherapy is then started without checking whether the treatment plan needs to be updated in view of the transformed actual position of the soft tissue body part. Rather, it may then after treatment be determined by way of forward planning of the actually administered dose whether the administered dose fulfills predetermined conditions in particular in view of the different body parts which have been irradiated. On that basis, it may then be determined whether the treatment plan needs to be updated for future treatment sessions (fractions).

The invention claimed is:

1. A radiotherapy system, comprising:
a radiation treatment device for treating a treatment body part of a patient's body with treatment radiation;
a patient positioning device for positioning the patient's body, the radiation treatment device constituted for treating a treatment body part when the patient is positioned on the patient positioning device for treatment;
a computer comprising at least one processor configured to execute a computer-implemented method for determining a change in a position of a soft tissue body part of a patient's body, the method comprising executing, on the processor, steps of:
acquiring, by the at least one processor, bony body part planned position data comprising bony body part planned position information describing a planned position of a bony body part of the patient's body;
acquiring, by the at least one processor, soft tissue body part planned position data comprising soft tissue body part planned position information describing a planned position of the soft tissue body part;
acquiring, by the at least one processor, bony body part actual position data comprising bony body part actual position information describing an actual position of the bony body part;
acquiring, by the at least one processor, soft tissue body part actual position data comprising soft tissue body part actual position information describing an actual position of the soft tissue body part;
determining, by the at least one processor and based on the bony body part planned position data and the bony body part actual position data, bony body part position transformation data comprising bony body part position transformation information describing a bony body part position transformation between the planned position and the actual position of the bony body part;
determining, by the at least one processor and based on the bony body part position transformation data and the soft tissue body part actual position data, soft tissue transformed actual position data comprising soft tissue transformed actual position information describing a transformed actual position of the soft tissue body part;
determining, by the at least one processor and based on the soft tissue transformed actual position data and the soft tissue body part planned position data, soft tissue body part position transformation data comprising soft tissue body part position transformation information describing a soft tissue body part position transformation between the planned position of the of the soft tissue body part and the transformed actual position of the soft tissue body part,
wherein the radiotherapy system further comprises
a medical imaging device constituted for generating medical image data which serves as a basis for acquiring the bony body part actual position data, when the patient is placed on the patient positioning device for treatment, and for outputting the medical image data to the computer.

2. A computer-implemented method for determining a change in a position of a soft tissue body part of a patient's body, the method comprising executing, on at least one processor of a computer, steps of:
acquiring, by the at least one processor, bony body part planned position data comprising bony body part planned position information describing a planned position of a bony body part of the patient's body;
acquiring, by the at least one processor, soft tissue body part planned position data comprising soft tissue body part planned position information describing a planned position of the soft tissue body part;
receiving from a medical imaging device generated medical image data obtained from a patient placed on a patient positioning device, the relative positions between the patient positioning device and a radiotherapy treatment device being controllable;

acquiring, by the at least one processor, bony body part actual position data based upon the medical imaging device generated medical image data comprising bony body part actual position information describing an actual position of the bony body part;

acquiring, by the at least one processor, soft tissue body part actual position data comprising soft tissue body part actual position information describing an actual position of the soft tissue body part;

determining, by the at least one processor and based on the bony body part planned position data and the bony body part actual position data, bony body part position transformation data comprising bony body part position transformation information describing a bony body part position transformation between the planned position and the actual position of the bony body part;

determining, by the at least one processor and based on the bony body part position transformation data and the soft tissue body part actual position data, soft tissue transformed actual position data comprising soft tissue transformed actual position information describing a transformed actual position of the soft tissue body part;

determining, by the at least one processor and based on the soft tissue transformed actual position data and the soft tissue body part planned position data, soft tissue body part position transformation data comprising soft tissue body part position transformation information describing a soft tissue body part position transformation between the planned position of the of the soft tissue body part and the transformed actual position of the soft tissue body part;

issuing control data based upon the soft tissue body part position transformation data to cause relative movement between the patient positioning device and the radiotherapy device.

3. The method according to claim 2, wherein the soft tissue body part position transformation is a rigid transformation.

4. The method according to claim 2, wherein the bony body part position transformation is a rigid transformation.

5. The method according to claim 2, wherein the bony body part planned position data and the soft tissue planned position data is acquired based on medical image data taken with a computer tomograph, and wherein the bony body part actual position data is acquired, at the processor, based on medical image data taken with a cone-beam computer tomograph or an x-ray device, and wherein the soft tissue body part actual position data is acquired, at the processor, based on medical image data taken with a cone-beam computer tomograph.

6. The method according to claim 2, further comprising executing, on the processor of the computer, steps of:

determining, by the processor, actual dose distribution data comprising actual dose distribution information describing an actual distribution of an irradiation dose in the patient's body when the soft tissue body part has its transformed actual position;

determining, by the processor, whether the actual dose distribution fulfills a predetermined condition.

7. The method according to claim 6, wherein, if it is determined that the predetermined condition is not fulfilled, patient positioning device control data comprising patient positioning device control information describing a control signal for moving the patient's body is determined, by the processor, based on the soft tissue body part position transformation data.

8. The method according to claim 6, wherein, if it is determined that the predetermined condition is fulfilled, irradiation control data comprising irradiation control information is determined, by the processor, which indicates that irradiation is to be started.

9. The method according to claim 2, further comprising executing, on the processor of the computer, steps of:

acquiring, at the processor, planned dose distribution data comprising planned dose distribution information describing a planned distribution of an irradiation dose in the patient's body when the soft tissue body part has its planned position;

determining, by the processor, actual dose distribution data comprising actual dose distribution information describing an actual distribution of an irradiation dose in the patient's body when the soft tissue body part has its actual position;

determining, by the processor and based on comparing the planned dose distribution information and the actual dose distribution information, whether the result of comparing the planned distribution of an irradiation dose and the actual distribution of an irradiation fulfills a predetermined condition.

10. The method according to claim 9, wherein, if it is determined that the predetermined condition is not fulfilled, the planned dose distribution data is updated, by the processor, based on the soft tissue body part position transformation data.

11. The method according to claim 2, wherein at least one of the soft tissue body part position transformation data and the soft tissue transformed actual position data is saved in a non-transitory memory device.

12. A non-transitory computer-readable program storage medium storing a program which, when running on at least one processor of a computer or when loaded into a memory of the computer, causes the computer to perform a computer-implemented method for determining a change in a position of a soft tissue body part of a patient's body, the method comprising executing, on the processor of the computer, steps of:

acquiring, by the at least one processor, bony body part planned position data comprising bony body part planned position information describing a planned position of a bony body part of the patient's body, acquiring, by the at least one processor, soft tissue body part planned position data comprising soft tissue body part planned position information describing a planned position of the soft tissue body part;

receiving from a medical imaging device generated medical image data obtained from a patient placed on a patient positioning device, the relative positions between the patient positioning device and a radiotherapy treatment device being controllable;

acquiring, by the at least one processor, bony body part actual position data based upon the medical imaging device generated medical image data comprising bony body part actual position information describing an actual position of the bony body part;

acquiring, by the at least one processor, soft tissue body part actual position data comprising soft tissue body part actual position information describing an actual position of the soft tissue body part;

determining, by the at least one processor and based on the bony body part planned position data and the bony body part actual position data, bony body part position transformation data comprising bony body part position transformation information describing a bony body part position transformation between the planned position and the actual position of the bony body part;

determining, by the at least one processor and based on the bony body part position transformation data and the soft tissue body part actual position data, soft tissue transformed actual position data comprising soft tissue transformed actual position information describing a transformed actual position of the soft tissue body part;

determining, by the at least one processor and based on the soft tissue transformed actual position data and the soft tissue body part planned position data, soft tissue body part position transformation data comprising soft tissue body part position transformation information describing a soft tissue body part position transformation between the planned position of the of the soft tissue body part and the transformed actual position of the soft tissue body part;

issuing control data based upon the soft tissue body part position transformation data to cause relative movement between the patient positioning device and the radiotherapy treatment device.

13. A computer comprising the program storage medium according to claim 12.

14. A computer-implemented method for determining a change in a position of a soft tissue body part of a patient's body, the method comprising executing, on at least one processor of a computer, steps of:

acquiring, by the at least one processor, bony body part planned position data comprising bony body part planned position information describing a planned position of a bony body part of the patient's body;

acquiring, by the at least one processor, soft tissue body part planned position data comprising soft tissue body part planned position information describing a planned position of the soft tissue body part;

receiving from a medical imaging device generated medical image data obtained from a patient placed on a patient positioning device, the relative positions between the patient positioning device and a radiotherapy treatment device being controllable;

acquiring, by the at least one processor, bony body part actual position data based upon the medical imaging device generated medical image data comprising bony body part actual position information describing an actual position of the bony body part;

acquiring, by the at least one processor, soft tissue body part actual position data comprising soft tissue body part actual position information describing an actual position of the soft tissue body part;

determining, by the at least one processor and based on the bony body pan planned position data and the bony body part actual position data, bony body part position transformation data comprising bony body part position transformation information describing a bony body part position transformation between the planned position and the actual position of the bony body part;

determining, by the at least one processor and based on the bony body part position transformation data and the soft tissue body part actual position data, soft tissue transformed actual position data comprising soft tissue transformed actual position information describing a transformed actual position of the soft tissue body part;

determining, by the at least one processor and based on the soft tissue transformed actual position data and the soft tissue body part planned position data, soft tissue body part position transformation data comprising soft tissue body part position transformation information describing a soft tissue body part position transformation between the planned position of the of the soft tissue body part and the transformed actual position of the soft tissue body part;

issuing control data to cause a change in the relative position between a set arrangement of a beam position emitted from the radiotherapy treatment device and a target region having a treatment body part which is to be treated by the radiotherapy treatment device.

* * * * *